United States Patent [19]
Tang et al.

[11] Patent Number: 6,130,064
[45] Date of Patent: Oct. 10, 2000

[54] HUMAN SMN-LIKE PROTEIN

[75] Inventors: Y. Tom Tang, San Jose; Neil C. Corley, Mountain View; Karl J. Guegler, Menlo Park, all of Calif.

[73] Assignee: Incyte Pharmaceuticals, Inc., Palo Alto, Calif.

[21] Appl. No.: 09/028,327

[22] Filed: Feb. 24, 1998

[51] Int. Cl.$^7$ ..................................................... C12N 15/12
[52] U.S. Cl. .................... 435/69.1; 536/23.5; 435/320.1; 435/225; 435/252.3
[58] Field of Search ............................... 536/23.5; 435/6, 435/320.1, 325, 325.3, 69.1

[56] References Cited

FOREIGN PATENT DOCUMENTS

| | | |
|---|---|---|
| 0708178A | 4/1996 | European Pat. Off. . |
| 0711833A | 5/1996 | European Pat. Off. . |

OTHER PUBLICATIONS

Lefebvre, S., et al., "Identification and Characterization of a Spinal Muscular Atrophy–Determining Gene," *Cell*, 80:155–165 (1995).

Burglen, L., et al., "Structure and Organization of the Human Survival Motor Neurone (SMN) Gene," *Genomics*, 32:479–482 (1996).

Coovert, D., et al., "The survival motor neuron protein in spinal muscular atrophy," *Human Molecular Genetics*, 6(8):1205–1214 (1997).

Liu, Q. And Dreyfuss, G., "A Novel nuclear structure containing the survival of motor neurons protein," *The Embo Journal*, 15(14):3555–3565 (1996).

Viollet, L., et al., "cDNA Isolation, Expression, and Chromosomal Localization of the Mouse Survival Motor Neuron Gene (Smn)," *Genomics*, 40:185–188 (1997) (GI 1857114 & GI 1857113).

Schrank, B., et al., "Inactivation of the survival motor neuron gene, a candidate gene for human spinal muscular atrophy, leads to massive cell death in early mouse embryos," *Proc. Natl. Acad. Sci.*, 94:9920–9925 (1997).

Viollet, L., et al., (GI 1857114), GenBank Sequence Database (Accession U63294), National Center for Biotechnology Information, National Library of Medicine, Bethesda, Maryland 20894.

Violett, L., et al., (GI 1857113), GenBank Sequence Database (Accession U63294), National Center for Biotechnology Information, National Library of Medicine, Bethesda, Maryland 20894.

Burglen, L., et al., (GI 1314346), GenBank Sequence Database (Accession U43876), National Center for Biotechnology Information, National Library of Medicine, Bethesda, Maryland 20894.

Burglen, L., et al., (GI 1314337), GenBank Sequence Database (Accession U43876), National Center for Biotechnology Information, National Library of Medicine, Bethesda, Maryland 20894.

EMBL/GenBank Databases Accession No. Z78358 Sequence reference HSZ78358 Aug. 16, 1996, Neri, C. et al: "Survey of CAG/CTG repeats in human cDNAs representing new genes: candidates for inherited neurological diseases", XP002106944.

Neri, C. et al., "Survey of CAG/CTG repeats in human cDNAs representing new genes: candidates for inherited neurological disorders", *Human Molecular Genetics*, vol. 5, No. 7, Jul. 1, 1996, pp. 1001–1009, XP000673216.

EMBL/GenBank Databases Accession No. T91668 Sequence reference HS66857, Apr. 11, 1995, Hillier, L. et al: "The WashU–Merck EST Project", XP002106945.

Neubauer, G. et al., "Mass spectrometry and EST–database searching allows characterization of the multi–protein spliceosome complex", *Nature Genetics*, vol. 20, Sep. 1998, pp. 46–50, XP002106943.

EMBL–GenBank Databases Accession No. AF083385 Sequence reference AF083385, Oct. 16, 1998, Neubauer, G. et al: "Mass spectrometry and EST–database searching allows characterization of the multi–protein spliceosome complex", XP002106946.

EMBL/GenBank Databases Accession No. AF107463 Sequence reference AF107463, Dec. 11, 1998, Chen, J. et al: "Isolating and cloning HSP cDNA", XP002106947.

EMBL/GenBank Databases Accession No. AI182770 Sequence reference AI182770, Oct. 13, 1998, Marra, M. et al: "The WashU–HHMI Mouse EST project", XP002106948.

Genbank Accession No. N22328, Dec. 1995.

Genbank Accession No. AA180296, Dec. 1996.

*Primary Examiner*—Marianne P. Allen
*Attorney, Agent, or Firm*—Incyte Pharmaceuticals, Inc.

[57] ABSTRACT

The invention provides a human SMN-like protein (HSLP) and polynucleotides which identify and encode HSLP. The invention also provides expression vectors, host cells, antibodies, agonists, and antagonists. The invention also provides methods for treating or preventing disorders associated with expression of HSLP.

7 Claims, 8 Drawing Sheets

```
                     9              18              27              36              45              54
5' TCT TTC ATA GAG ACT AAA GTT ATT CAG CAG GCA AAA TAA TCT ACT TAA GTC
                    63              72              81              90              99             108
   CTG CCT TTC TTT TTT CAC TTA AAA AAG TGG GTG TGA TAA TAT CCA GGC TAG CTA
                   117             126             135             144             153             162
   GCT GAC TAG CTC CCC GGG CAG TCT ATG ATA ATC AGA GAT AGT CAA TTT ATT AGG
                   171             180             189             198             207             216
   CTG TTT TGC TGA ATA AGC TGG TTC TAA AGG AGG CAG GGG TCA AGT CAC TTG TCT
                   225             234             243             252             261             270
   CAT ATA TTA CAG TGG CTC TCT GCA TCC CCG AAA CGC CTT CCT TCA GTA AGC AGA
                   279             288             297             306             315             324
   GTG CTT GAG TGC ACC CCA TTT GAC CTG CTG ATA TGT AGA TCA CAA CNC CTG ATG
                   333             342             351             360             369             378
   CTT CCT GGA ATT GCC GAT TAC TGT AAC TGC TGC CCA TCT GTC GAT GAA GGA GCA
                   387             396             405             414             423             432
   GTT TCA GAA CTC AGA CTT GAG GGA AAA GTA ATT AAT GGT GCC CGG CGT TCC
                   441             450             459             468             477             486
   TCC CTT CCC CCT CGC CGC CGA CCG AGT TCT TCC TTT TCA GAC CGG GTC GCC TTG
```

FIGURE 1A

```
      495              504              513              522              531              540
CTG   TCG   CGG   TGA   TTT   TCC   TGC   TAC   TGC   TGC   TGC   CAC   CGC   CAC 549              558              567              576              585              594
TAC   CAC   TGG   GCT   CAT   TTG   CCC   CGA   CCC   CTT   CCC   GCC   CCG   CCA   GCC   CCA 603              612              621              630              639              648
CAC   AAG   ATG   TCA   GAG   TTA   GCA   AAG   CAG   CTG   GCA   AGC   TAC   AAA   GCT   CAG   CTC
      Q    K    M    S    E    L    A    K    Q    L    A    S    Y    K    A    Q    L 657              666              675              684              693              702
CAG   CAA   GTT   GAA   GCT   GCA   TTA   TCT   GGA   AAT   GGA   GAA   CTA   TTG   GAT   TTG   AAA
Q    Q    V    E    A    A    L    S    G    N    G    E    N    E    L    L    D    L    K 711              720              729              738              747              756
TTG   AAG   GAT   TTA   CAA   GAA   GTT   ATA   GAA   CTA   ACC   AAA   GAC   CTT   CTG   TCA   ACT
L    K    D    L    Q    E    V    I    E    L    T    K    D    L    L    S    T 765              774              783              792              801              810
CAA   CCT   TCT   GAG   ACG   CTT   GCA   AGT   TCA   GAC   AGT   TTT   GCT   TCT   ACT   CAA   CCT   ACT
Q    P    S    E    T    L    A    S    S    D    S    F    A    S    T    Q    P    T 819              828              837              846              855              864
CAT   TCA   TGG   AAA   GTA   GGA   GAC   AAG   TGT   ATG   GCA   GTC   TGG   AGT   GAA   GAT   GGA   CAG
H    S    W    K    V    G    D    K    C    M    A    V    W    S    E    D    G    Q
```

FIGURE 1B

```
        873               882           891           900           909           918
TGT TAT GAA GCG GAG ATT GAG GAG ATA GAT GAA GAA AAT GGC ACC GCT GCA ATC
 C   Y   E   A   E   I   E   E   I   D   E   E   N   G   T   A   A   I 927               936           945           954           963           972
ACC TTT GCT GGT TAT GGC AAT GCT GAA GTG ACT CCA CTG TTG AAC CTC AAG CCT
 T   F   A   G   Y   G   N   A   E   V   T   P   L   L   N   L   K   P 981               990           999          1008          1017          1026
GTA GAA GAA AGG AAG GCA AAG GAC AGT GGC AAC CCC ATG TCA AAA
 V   E   E   R   K   A   K   D   S   G   N   K   P   M   S   K 1035              1044          1053          1062          1071          1080
AAA GAA ATG ATT GCC CAG CAG CGT GAA TAT AAA GGC AAC AAA AAG AAA GCT TTG AAA AAA
 K   E   M   I   A   Q   Q   R   E   Y   K   G   N   K   K   K   A   L   K   K 1089              1098          1107          1116          1125          1134
GCT CAG AGA ATA AAA GAA CTT GAG CAG GAA AGA GAC CAG GAA AAA GTG AAA TGG
 A   Q   R   I   K   E   L   E   Q   E   R   E   D   Q   E   K   V   K   W 1143              1152          1161          1170          1179          1188
CAA CAA TTC AAC AGA GCC TAT TCT AAA AAC AAA AAA AAA GGC CAG GTA AAG AGG
 Q   Q   F   N   R   A   Y   S   K   N   K   K   K   G   Q   V   K   R 1197              1206          1215          1224          1233          1242
AGT ATT TTT GCT TCA CCT GAG AGT GTG ACT GGT AAA GTT GGA GTA GGA ACC TGT
 S   I   F   A   S   P   E   S   V   T   G   K   V   G   V   G   T   C
```

FIGURE 1C

```
            1251       1260       1269       1278       1287       1296
GGA ATT GCT GAT AAA CCT ATG ACA CAA TAT CAA GAT ACC TCT AAA TAC AAT GTC
 G   I   A   D   K   P   M   T   Q   Y   Q   D   T   S   K   Y   N   V 1305       1314       1323       1332       1341       1350
AGG CAT TTG ATG CCT CAA TAA TCA GAA AAA CTG TTG GAT TTC ATC TCT GCA GGG
 R   H   L   M   P   Q 1359       1368       1377       1386       1395       1404
CTT TAC ATT TAC CTT TTT ATC CTT ATA TTT TTC TAA AGG TAA ATT ATT TGT TAG 1413       1422       1431       1440       1449       1458
ATG AGT AAG CAA GAT ACC ATT GTC ATT GGT TGG CTT CAG TAG AAT GAA ACG 1467       1476       1485       1494       1503       1512
TGA AGA AAT TGC ATT TGA TAA CTG CTA TTC ATT TAA CTT TCA TTC TCA GTA 1521       1530       1539       1548       1557       1566
CCA CGG TTC CCT CAA AGT TTG TTG AAT AAA GCA ACT TTT GTA GAT GCT GTT TCA 1575       1584       1593       1602       1611       1620
TAC AGC ACT TAG ATG AAT TAT TGA TCT TCC TAA TAT CAG GCG CCT ACT TAA CCT 1629       1638       1647       1656       1665       1674
ATG GTG TGT ACT TTT TGT AAG TTG TAA CTT GAA ATT TTC AGA TGC TTT GAA CTT
```

FIGURE 1D

```
         1683      1692      1701      1710      1719      1728
         GAC ACA TAC TCT AGC AAT TCA TTG GAA CAC CAA GGC AAA AAC ACC AAC CTG CTA
         1737      1746      1755      1764      1773      1782
         AAA GAG ATC TTT TCA TTT TTC TTA TTT TCA GCT TTA AAA CTT AGC TGT CGT TCA
         1791      1800      1809      1818      1827      1836
         GTT AAG CTT AAA GAT AGG TTA ATT TGT AAA TGG CAA AGT TTG TTT TGA GGT TTT
         1845      1854      1863      1872      1881      1890
         TCC TCA ATA ACT TGT TTC CCA GGC CTA TTA GGC CAT CTC TAA AAT TGA TCT AGC
         1899      1908      1917      1926      1935      1944
         TGT TTT ATT TTT ATG TAC TCT TAG TAT GTA AGA AAC CTT AGG ATG AGC TCC
         1953      1962      1971      1980      1989      1998
         CTT TTC TAA GGT GTT TTT GTT TTT TGT ATG TTT GCT TTT TTC CTG TTT TTT GTT
         2007      2016      2025      2034      2043      2052
         TTT TCC ATT TAC GGC AGT GGT ACC ATG TTT TGG ATG TGT GAT GTT TAT ATG GGA
         2061      2070      2079      2088      2097      2106
         GAA CAA AAA GCT GAT GTA TAG CCC TGT ATA CAG TGT AGA TAC TAT TTT TGT AAA
         2115      2124      2133      2142      2151      2160
         AAC ACA AGG CTA AAT TAA TGA ACA AGA ATA CTG AAT ATT TCA TCA TTA AAA ATT
```

FIGURE 1E

```
                2169              2178              2187              2196              2205              2214
            TCT TGT ATT       TCT TGT GCA       TTA ATC TGA       CGA TAA TTT       CCC TGT ATA       TTA TGT TCA 2223              2232              2241              2250              2259              2268
            TTT AGC TGT       TTG TAA TTT       TTG TTA ATT       AGA TCA GGT       TGT CTG CAT       TTG TTG GTG 2277              2286              2295              2304              2313              2322
            TAA GTG AAC       ATC ATC ACA       GTT ATC CTG       AGT TGA GTT       TAA GCC AAA       TAC ATG CAT 2331              2340              2349              2358              2367              2376
            AGA AAA GGG       TCT TCC TAT       TAA TGG AAG       AAG GTA ATT       TTT AGG ATG       TGT ATT ATT 2385              2394              2403              2412              2421
            TCA GTT TTG       TAT GTT TAA       CTT TTA TTA       AAT AAA GTG       TTT TTA AAA       TCT CC 3'
```

```
1    MSEDLAKQLASYKAQLQQV---EAALSGN                3769729
1    MAMGSGGAGS---EQEDTVLFRRGTGQSDD                GI 1857114
1    MAMSSGGSGGGVPEQEDSVLFRRGTGQSDD                GI 1314346

27   GENEDLLKLKKDLQEVIE-LTKDLLSTQPS                3769729
28   SDIWDDTALIKAYDKAVASFKHALKNGDIC                GI 1857114
31   SDIWDDTALIKAYDKAVASFKHALKNGDIC                GI 1314346

56   ETLASSDSFASTQPT-------H                       3769729
58   ETPDKPKGTARRKPAKKNKSQKKNATTPLK                GI 1857114
61   ETSGKPKTTPKRKPAKKNKSQKKNTAASLQ                GI 1314346

72   SWKVGDKCMAVWSEDGQCYEAEIEEIDEEN                3769729
88   QWKVGDKCSAVWSEDGCIYPATHTSIDFKR                GI 1857114
91   QWKVGDKCSAIWSEDGCIYPATHASIDFKR                GI 1314346

102  GTAAITFAGYGNAEVTPLLNL-KPVEEGRK                3769729
118  ETCVVVYTGYGNREEQNLSDLLSPTCEVAN                GI 1857114
121  ETCVVVYTGYGNREEQNLSDLLSPICEVAN                GI 1314346

131  AKEDSGNKPMSKKEMIAQQREYKKKKALKK                3769729
148  STEQNTQENE--SQVSTDDSE-HSSRSLRS                GI 1857114
151  NIEQNAQENENESQVSTDESE-NSRSPGNK                GI 1314346
```

```
161 AQRIKELEQEREDQKVKWQQF---NNRAYSK              3769729
175 KAHSKS---------KAAPWTSFLPPPPMPG              GI 1857114
180 SDNIKP---------KSAPWNSFLPPPPMPG              GI 1314346

189 NKKGQVKRSI-FASPESVTG-----------              3769729
198 SGLGPKPGLKFNGPPPPPLPPPPFLPCW                 GI 1857114
203 PRLGPKPGLKFNGPPPPPPPPPHLLSCW                 GI 1314346

208 --KVGVGTCGIADKP----------------              3769729
228 MPPFFPSGPPIHPPPPISPDCLDDTDALGS               GI 1857114
233 LPPFFPSGPPIHPPPPICPDSLDDADALGS               GI 1314346

221 ---MTQYQDTSKYNVRHLMPQ----------              3769729
258 MLISWYMSGYHTGYYMGFRQNKKEGKCSHT               GI 1857114
263 MLISWYMSGYHTGYYMGFRQNQKEGRCSHS               GI 1314346

HUMAN SMN-LIKE PROTEIN

FIELD OF THE INVENTION

This invention relates to nucleic acid and amino acid sequences of a human SMN-like protein and to the use of these sequences in the diagnosis, treatment, and prevention of neurological, reproductive, and cell proliferative disorders.

BACKGROUND OF THE INVENTION

Motor neurons directly control muscle activity throughout the body. Motor neuron fibers that extend from the spinal cord to the muscle transmit neural impulses. Motor neuron cell bodies lie within gray matter, the inner core of the spinal cord. They are confined to the anterior horn, one of three distinct functional regions of gray matter. The motor neuron cell bodies receive signals primarily from neurons contained in the other two regions of gray matter. These neurons transmit signals from the brain and other regions of the spinal cord.

Spinal muscular atrophy (SMA) is a fatal neurodegenerative disorder that specifically affects motor neurons of the anterior horn. Extensive loss of these neurons results in progressive muscle weakness and paralysis leading to muscular atrophy. SMA is an autosomal recessive disorder that occurs once in every 6000 live births and has a carrier frequency of 1 in 40. Cystic fibrosis is the only fatal autosomal recessive disorder that occurs with greater frequency. SMA afflicts children, and three types of SMA have been classified based on age of onset and clinical course of the disease. Type I, also called infantile SMA or Werdnig-Hoffman disease, is the most severe form with onset before six months of age and death from respiratory failure by two years of age. Type II, also called chronic childhood SMA or intermediate SMA, presents at around 18 months of age and progresses slowly. Afflicted children cannot walk unaided but survive beyond four years of age. Type III, also called Wohlfart-Kugelberg-Welander disease, is the mildest form with onset ranging from two years of age to adolescence and variable degrees of muscular weakness. (Lefebvre, S. et al. (1995) Cell 80:155–165.)

SMA is caused by lesions in the survival motor neuron (SMN) gene on chromosome 5q13. (Burglen, L. et al. (1996) Genomics 32:479–482.) The normal chromosome 5 contains a duplication of the SMN locus, resulting in a telomere proximal SMN gene ($SMN^T$) and a centromere proximal SMN gene ($SMN^C$). The two genes are nearly identical in nucleotide sequence, and both encode a 294-amino acid protein of 38 kilodaltons. However, the $SMN^C$ RNA transcript can also be alternatively spliced, and the resultant protein is truncated at the C-terminus. The function of this alternative protein product is unknown. Molecular genetic analysis indicates that in over 98% of patients with SMA, $SMN^T$ is completely or partially deleted. In the remaining 2%, $SMN^T$ contains point mutations or alterations in splice site consensus sequences. In addition, the severity of the lesion in $SMN^T$ is correlated with the clinical severity of SMA. These data indicate that $SMN^T$, and not $SMN^C$, plays a critical role in the determination of SMA. (Lefebvre, S. et al. supra.) However, some studies indicate that the activity of $SMN^C$ may modulate the clinical severity of SMA as previously established by defects in $SMN^T$. (Coovert, D. D. et al. (1997) Hum. Mol. Genet. 6:1205–1214.) In general, detection of lesions in $SMN^T$ may provide the basis for definitive prenatal and childhood diagnosis of SMA.

Quantitative western analysis shows that SMN protein is normally expressed at high levels not only in the spinal cord, but also in the kidney, liver, and brain. Intermediate SMN levels are detected in skeletal and cardiac muscle, and low levels are detected in primary fibroblasts and lymphoblasts. The role, if any, for SMN outside of the spinal cord is unclear, as the pathology of SMA is specific to motor neuron muscle control. (Coovert et al. supra.) At the cellular level, immunocytochemistry demonstrates that SMN is localized to both the cytoplasm and the nucleus. SMN is diffusely distributed throughout the cytoplasm, while nuclear SMN is concentrated at discrete foci. These foci, called gems, are novel structures that are intimately associated with coiled bodies. Coiled bodies are subnuclear structures involved in RNA processing and metabolism. An in vivo screen for SMN-interacting polypeptides identified fibrillarin, a known component of coiled bodies, and the RGG RNA-binding motif of hnRNP U, a nuclear protein involved in RNA processing. These data suggest that the molecular basis of SMA may involve defects in RNA processing in motor neurons. (Liu, Q. and Dreyfuss, G. (1996) EMBO J. 15:3555–3565.)

The mouse homolog of SMN has been cloned and localized to chromosome 13 in a region syntenic to that of human chromosome 5q13. Unlike human SMN, mouse SMN (mSMN) is a single-copy gene, suggesting that duplication of the human locus is a recent evolutionary event. mSMN encodes a 288-amino acid protein that shares 82% amino acid identity with human SMN. Northern analysis shows that mSMN RNA is widely expressed in various tissues, including heart, brain, kidney and testis. (Viollet, L. et al. (1997) Genomics 40:185–188.) Homozygous deletion of mSMN is lethal during the morula (16–64 cell) stage of embryogenesis. This phenotype is much more severe than that of SMA in humans, suggesting that differences in gene copy number may influence the severity of the SMA phenotype. In humans, $SMN^C$ may partially compensate for deletion of $SMN^T$ to delay disease onset and prolong survival. (Schrank, B. et al. (1997) Proc. Natl. Acad. Sci. USA 94:9920–9925.)

The discovery of a new human SMN-like protein and the polynucleotides encoding it satisfies a need in the art by providing new compositions which are useful in the diagnosis, treatment, and prevention of neurological, reproductive, and cell proliferative disorders.

SUMMARY OF THE INVENTION

The invention is based on the discovery of a human SMN-like protein, HSLP, which shows homology to mouse and human SMN, a protein involved in motor neuron survival. The invention features a substantially purified polypeptide comprising the amino acid sequence of SEQ ID NO:1 or a fragment of SEQ ID NO:1.

The invention further provides a substantially purified variant having at least 90% amino acid sequence identity to the amino acid sequence of SEQ ID NO:1 or a fragment of SEQ ID NO:1. The invention also provides an isolated and purified polynucleotide encoding the polypeptide comprising the sequence of SEQ ID NO:1 or a fragment of SEQ ID NO:1. The invention also includes an isolated and purified polynucleotide variant having at least 90% polynucleotide sequence identity to the polynucleotide encoding the polypeptide comprising the amino acid sequence of SEQ ID NO:1 or a fragment of SEQ ID NO:1.

The invention further provides an isolated and purified polynucleotide which hybridizes under stringent conditions to the polynucleotide encoding the polypeptide comprising the amino acid sequence of SEQ ID NO:1 or a fragment of SEQ ID NO:1, as well as an isolated and purified polynucleotide which is complementary to the polynucleotide encoding the polypeptide comprising the amino acid sequence of SEQ ID NO:1 or a fragment of SEQ ID NO:1.

The invention also provides an isolated and purified polynucleotide comprising the polynucleotide sequence of SEQ ID NO:2 or a fragment of SEQ ID NO:2, and an isolated and purified polynucleotide variant having at least 90% polynucleotide sequence identity to the polynucleotide comprising the polynucleotide sequence of SEQ ID NO:2 or a fragment of SEQ ID NO:2. The invention also provides an isolated and purified polynucleotide having a sequence complementary to the polynucleotide comprising the polynucleotide sequence of SEQ ID NO:2 or a fragment of SEQ ID NO:2. The invention also provides a polynucleotide fragment comprising nucleotides 712–747 for detecting the presence or expression of an identical endogenous gene.

The invention further provides an expression vector containing at least a fragment of the polynucleotide encoding the polypeptide comprising the sequence of SEQ ID NO:1 or a fragment of SEQ ID NO:1. In another aspect, the expression vector is contained within a host cell.

The invention also provides a method for producing a polypeptide comprising the amino acid sequence of SEQ ID NO:1 or a fragment of SEQ ID NO:1, the method comprising the steps of: (a) culturing the host cell containing an expression vector containing at least a fragment of a polynucleotide encoding the polypeptide comprising the amino acid sequence of SEQ ID NO:1 or a fragment of SEQ ID NO:1 under conditions suitable for the expression of the polypeptide; and (b) recovering the polypeptide from the host cell culture.

The invention also provides a pharmaceutical composition comprising a substantially purified polypeptide having the sequence of SEQ ID NO:1 or a fragment of SEQ ID NO:1 in conjunction with a suitable pharmaceutical carrier.

The invention further includes a purified antibody which binds to a polypeptide comprising the sequence of SEQ ID NO:1 or a fragment of SEQ ID NO:1, as well as a purified agonist and a purified antagonist of the polypeptide.

The invention also provides a method for treating or preventing a neurological disorder, the method comprising administering to a subject in need of such treatment an effective amount of a pharmaceutical composition comprising substantially purified polypeptide having the amino acid sequence of SEQ ID NO:1 or a fragment of SEQ I) NO:1.

The invention also provides a method for treating or preventing a reproductive disorder, the method comprising administering to a subject in need of such treatment an effective amount of a pharmaceutical composition comprising substantially purified polypeptide having the amino acid sequence of SEQ ID NO:1 or a fragment of SEQ ID NO:1.

The invention also provides a method for treating or preventing a cell proliferative disorder, the method comprising administering to a subject in need of such treatment an effective amount of an antagonist of the polypeptide having the amino acid sequence of SEQ ID NO:1 or a fragment of SEQ ID NO:1.

The invention also provides a method for detecting a polynucleotide encoding a polypeptide comprising the amino acid sequence of SEQ ID NO:1 or a fragment of SEQ ID NO:1 in a biological sample containing nucleic acids, the method comprising the steps of: (a) hybridizing the complement of the polynucleotide encoding the polypeptide comprising the amino acid sequence of SEQ ID NO:1 or a fragment of SEQ ID NO:1 to at least one of the nucleic acids of the biological sample, thereby forming a hybridization complex; and (b) detecting the hybridization complex, wherein the presence of the hybridization complex correlates with the presence of a polynucleotide encoding the polypeptide comprising the amino acid sequence of SEQ ID NO:1 or a fragment of SEQ ID NO:1 in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, 1D, 1E, and 1F show the amino acid sequence (SEQ ID NO:1) and nucleic acid sequence (SEQ ID NO:2) of HSLP. The alignment was produced using MacDNASIS PRO™ software (Hitachi Software Engineering Co. Ltd., San Bruno, Calif.).

FIGS. 2A and 2B show the amino acid sequence alignments among HSLP (3769729; SEQ ID NO:1), mouse SMN (GI 1857114; SEQ ID NO:3), and human SMN (GI 1314346; SEQ ID NO:4), produced using the multisequence alignment program of DNASTAR™ software (DNASTAR Inc, Madison Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

Definitions

"HSLP," as used herein, refers to the amino acid sequences of substantially purified HSLP obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to HSLP, increases or prolongs the duration of the effect of HSLP. Agonists may include proteins, nucleic acids, carbohydrates, or any other molecules which bind to and modulate the effect of HSLP.

An "allele" or an "allelic sequence," as these terms are used herein, is an alternative form of the gene encoding HSLP. Alleles may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence. "Altered" nucleic acid sequences encoding HSLP, as described herein, include those sequences with deletions, insertions, or substitutions of different nucleotides, resulting in a polynucleotide the same HSLP or a polypeptide with at least one functional characteristic of HSLP. Included within this definition are polymorphisms which may or may not be readily detectable using a particular oligonucleotide probe of the polynucleotide encoding HSLP, and improper or unexpected hybridization to alleles, with a locus other than the normal chromosomal locus for the polynucleotide sequence encoding HSLP. The encoded protein may also be "altered," and may contain deletions, insertions, or substitutions of amino acid residues which produce a silent change and result in a functionally equivalent HSLP. Deliberate amino acid substitutions may be made on the basis of similarity in polarity, charge, solubility, hydrophobicity, hydrophilicity, and/or the amphipathic nature of the residues, as long as the biological or immunological activity of HSLP is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments", "immunogenic fragments", or "antigenic fragments" refer to fragments of HSLP which are preferably about 5 to about 15 amino acids in length and which retain some biological activity or immunological activity of HSLP. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual*, Cold Spring Harbor Press, Plainview, N.Y., pp.1–5.) The term "antagonist," as it is used herein, refers to a molecule which, when bound to HSLP, decreases the amount or the duration of the effect of the biological or immunological activity of HSLP. Antagonists may include proteins, nucleic acids, carbohydrates, antibodies, or any other molecules which decrease the effect of HSLP.

As used herein, the term "antibody" refers to intact molecules as well as to fragments thereof, such as Fa, F(ab')$_2$, and Fv fragments, which are capable of binding the epitopic determinant. Antibodies that bind HSLP polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to a specific nucleic acid sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic HSLP, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation, an aqueous solution, or a sterile composition. Compositions comprising polynucleotide sequences encoding HSLP or fragments of HSLP may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS), and other components (e.g., Denhardt's solution, dry milk, salmon sperm DNA, etc.).

The phrase "consensus sequence," as used herein, refers to a nucleic acid sequence which has been resequenced to resolve uncalled bases, extended using XL-PCR™ (Perkin Elmer, Norwalk, Conn.) in the 5' and/or the 3' direction, and resequenced, or which has been assembled from the overlapping sequences of more than one Incyte Clone using a computer program for fragment assembly, such as the GEL-VIEW™ Fragment Assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding HSLP, by northern analysis is indicative of the presence of nucleic acids encoding HSLP in a sample, and thereby correlates with expression of the transcript from the polynucleotide encoding HSLP.

A "deletion," as the term is used herein, refers to a change in the amino acid or nucleotide sequence that results in the absence of one or more amino acid residues or nucleotides.

The term "derivative," as used herein, refers to the chemical modification of HSLP, of a polynucleotide sequence encoding HSLP, or of a polynucleotide sequence complementary to a polynucleotide sequence encoding HSLP. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "homology," as used herein, refers to a degree of complementarity. There may be partial homology or complete homology. The word "identity" may substitute for the word "homology." A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (Southern or northern blot, solution hybridization, and the like) under conditions of reduced stringency. A substantially homologous sequence or hybridization probe will compete for and inhibit the binding of a completely homologous sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% homology or identity). In the absence of non-specific binding, the substantially homologous sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MegAlign program (DNASTAR, Inc., Madison Wis.). The MegAlign program can create alignments between two or more sequences according to different methods, e.g., the Clustal method. (See, e.g., Higgins, D. G. and P. M. Sharp (1988) Gene 73:237–244.) The Clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" as used herein, refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray," as used herein, refers to an arrangement of distinct polynucleotides arrayed on a substrate, e.g., paper, nylon or any other type of membrane, filter, chip, glass slide, or any other suitable solid support.

The terms "element" or "array element" as used herein in a microarray context, refer to hybridizable polynucleotides arranged on the surface of a substrate.

The term "modulate," as it appears herein, refers to a change in the activity of HSLP. For example, modulation may cause an increase or a decrease in protein activity, binding characteristics, or any other biological, functional, or immunological properties of HSLP.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are greater than about 60 nucleotides in length, and most preferably are at least about 100 nucleotides, at least about 1000 nucleotides, or at least about 10,000 nucleotides in length.

The terms "operably associated" or "operably linked," as used herein, refer to functionally related nucleic acid sequences. A promoter is operably associated or operably linked with a coding sequence if the promoter controls the transcription of the encoded polypeptide. While operably associated or operably linked nucleic acid sequences can be contiguous and in reading frame, certain genetic elements, e.g., repressor genes, are not contiguously linked to the encoded polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimer," "primer," "oligomer," and "probe," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation, and may be pegylated to extend their lifespan in the cell. (See, e.g., Nielsen, P. E. et al. (1993) Anticancer Drug Des. 8:53–63.)

The term "sample," as used herein, is used in its broadest sense. A biological sample suspected of containing nucleic acids encoding HSLP, or fragments thereof, or HSLP itself, may comprise a bodily fluid; an extract from a cell, chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotide sequences and the claimed polynucleotide sequences. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5× SSPE, 0.3% SDS, and 200 µg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of HSLP, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The Invention

The invention is based on the discovery of a new human SMN-like protein (HSLP), the polynucleotides encoding HSLP, and the use of these compositions for the diagnosis, treatment, or prevention of neurological, reproductive, and cell proliferative disorders.

Nucleic acids encoding the HSLP of the present invention were first identified in Incyte Clone 3769729 from the breast tissue cDNA library (BRSTNOT24) using a computer search for amino acid sequence alignments. A consensus sequence, SEQ ID NO:2, was derived from the following overlapping and/or extended nucleic acid sequences: Incyte Clones 3769729 (BRSTNOT24), 637394 (NEUTGMT01), 2207558 (SINTFET03), 1643342 (HEARFET01), and 1272275 (TESTTUT02).

In one embodiment, the invention encompasses a polypeptide comprising the amino acid sequence of SEQ ID NO:1, as shown in FIGS. 1A, 1B, 1C, 1D, 1E, and 1F. HSLP is 238 amino acids in length and has a potential N-glycosylation site at $N_{101}$; a potential casein kinase II phosphorylation site at $S_{141}$; and five potential protein kinase C phosphorylation sites at $S_{11}$, $S_{72}$, $S_{141}$, $T_{206}$, and $T_{227}$. As shown in FIGS. 2A and 2B, HSLP has chemical and structural homology with SMN from mouse (GI 1857114) and from human (GI 1314346). In particular, HSLP and mouse SMN share 18% identity, and HSLP and human SMN share 17% identity. In addition, the regions of HSLP from $W_{73}$ to $D_{98}$ and from $G_{110}$ to $E_{127}$ are highly conserved among SMN proteins from three divergent mammalian species: human, mouse, and dog. For example, these two regions of HSLP share 73% and 47% identity, respectively, with the homologous regions of both mouse and human SMN. HSLP is similar in size to mouse and human SMN, which are 288 and 294 amino acids in length, respectively. A fragment of SEQ ID NO:2 from about nucleotide 712 to about nucleotide 747 is useful for distinguishing nucleotide sequences encoding HSLP from those encoding other known SMN-like proteins. Northern analysis shows the expression of this sequence in various libraries, at least 67% of which are associated with cell proliferation. In particular, 38% of libraries expressing HSLP are derived from reproductive tissue.

The invention also encompasses HSLP variants. A preferred HSLP variant is one which has at least about 80%, more preferably at least about 90%, and most preferably at least about 95% amino acid sequence identity to the HSLP amino acid sequence, and which contains at least one functional or structural characteristic of HSLP.

The invention also encompasses polynucleotides which encode HSLP. In a particular embodiment, the invention encompasses a polynucleotide sequence comprising the sequence of SEQ ID NO:2, which encodes an HSLP.

The invention also encompasses a variant of a polynucleotide sequence encoding HSLP. In particular, such a variant polynucleotide sequence will have at least about 80%, more preferably at least about 90%, and most preferably at least about 95% polynucleotide sequence identity to the polynucleotide sequence encoding HSLP. A particular aspect of the invention encompasses a variant of SEQ ID NO:2 which has at least about 80%, more preferably at least about 90%, and most preferably at least about 95% polynucleotide sequence identity to SEQ ID NO:2. Any one of the polynucleotide variants described above can encode an amino acid sequence which contains at least one functional or structural characteristic of HSLP.

It will be appreciated by those skilled in the art that as a result of the degeneracy of the genetic code, a multitude of polynucleotide sequences encoding HSLP, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HSLP, and all such variations are to be considered as being specifically disclosed.

Although nucleotide sequences which encode HSLP and its variants are preferably capable of hybridizing to the nucleotide sequence of the naturally occurring HSLP under appropriately selected conditions of stringency, it may be advantageous to produce nucleotide sequences encoding HSLP or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HSLP and its derivatives without altering the encoded amino acid sequences include the production of RNA transcripts having more desirable properties, such as a greater half-life, than transcripts produced from the naturally occurring sequence.

The invention also encompasses production of DNA sequences which encode HSLP and HSLP derivatives, or fragments thereof, entirely by synthetic chemistry. After production, the synthetic sequence may be inserted into any of the many available expression vectors and cell systems using reagents that are well known in the art. Moreover, synthetic chemistry may be used to introduce mutations into a sequence encoding HSLP or any fragment thereof.

Also encompassed by the invention are polynucleotide sequences that are capable of hybridizing to the claimed polynucleotide sequences, and, in particular, to those shown in SEQ ID NO:2, or a fragment of SEQ ID NO:2, under various conditions of stringency. (See, e.g., Wahl, G. M. and S. L. Berger (1987) Methods Enzymol. 152:399–407; and Kimmel, A. R. (1987) Methods Enzymol. 152:507–511.)

Methods for DNA sequencing are well known and generally available in the art and may be used to practice any of the embodiments of the invention. The methods may employ such enzymes as the Klenow fragment of DNA polymerase I, Sequenase® (US Biochemical Corp., Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System (GIBCO/BRL, Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding HSLP may be extended utilizing a partial nucleotide sequence and employing various methods known in the art to detect upstream sequences, such as promoters and regulatory elements. For example, one method which may be employed, restriction-site PCR, uses universal primers to retrieve unknown sequence adjacent to a known locus. (See, e.g., Sarkar, G. (1993) PCR Methods Applic. 2:318–322.) In particular, genomic DNA is first amplified in the presence of a primer which is complementary to a linker sequence within the vector and a primer specific to a region of the nucleotide sequenc. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region. (See, e.g., Triglia, T. et al. (1988) Nucleic Acids Res. 16:8186.) The primers may be designed using commercially available software such as OLIGO 4.06 Primer Analysis software (National Biosciences Inc., Plymouth, Minn.) or another appropriate program to be about 22 to 30 nucleotides in length, to have a GC content of about 50% or more, and to anneal to the target sequence at temperatures of about 68° C. to 72° C. The method uses several restriction enzymes to generate a suitable fragment in the known region of a gene. The fragment is then circularized by intramolecular ligation and used as a PCR template.

Another method which may be used is capture PCR, which involves PCR amplification of DNA fragments adjacent to a known sequence in human and yeast artificial chromosome DNA. (See, e.g., Lagerstrom, M. et al. (1991) PCR Methods Applic. 1:111–119.) In this method, multiple restriction enzyme digestions and ligations may be used to place an engineered double-stranded sequence into an unknown fragment of the DNA molecule before performing PCR. Other methods which may be used to retrieve unknown sequences are known in the art. (See, e.g., Parker, J. D. et al. (1991) Nucleic Acids Res. 19:3055–3060.) Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable in that they will include more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and a charge coupled device camera for detection of the emitted wavelengths. Output/light intensity may be converted to electrical signal using appropriate software (e.g., Genotyper™ and Sequence Navigator™, Perkin Elmer), and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HSLP may be used in recombinant DNA molecules to direct expression of HSLP, or fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express HSLP.

As will be understood by those of skill in the art, it may be advantageous to produce HSLP-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter HSLP-encoding sequences for a variety of reasons including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding HSLP may be ligated to a heterologous sequence to encode a fusion protein. For example, to screen peptide libraries for inhibitors of HSLP activity, it may be useful to encode a chimeric HSLP protein that can be recognized by a commercially available antibody. A fusion protein may also be engineered to contain a cleavage site located between the HSLP encoding sequence and the heterologous protein sequence, so that HSLP may be cleaved and purified away from the heterologous moiety.

In another embodiment, sequences encoding HSLP may be synthesized, in whole or in part, using chemical methods well known in the art. (See, e.g., Caruthers, M. H. et al. (1980) Nucl. Acids Res. Symp. Ser. 215–223, and Horn, T. et al. (1980) Nucl. Acids Res. Symp. Ser. 225–232.) Alternatively, the protein itself may be produced using chemical methods to synthesize the amino acid sequence of HSLP, or a fragment thereof. For example, peptide synthesis can be performed using various solid-phase techniques. (See, e.g., Roberge, J. Y. et al. (1995) Science 269:202–204.) Automated synthesis may be achieved using the ABI 431A Peptide Synthesizer (Perkin Elmer). Additionally, the amino acid sequence of HSLP, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1983) *Proteins, Structures and Molecular Properties*, W. H. Freeman and Co., New York, N.Y.)

In order to express a biologically active HSLP, the nucleotide sequences encoding HSLP or derivatives thereof may be inserted into appropriate expression vector, i.e., a vector which contains the necessary elements for the transcription and translation of the inserted coding sequence.

Methods which are well known to those skilled in the art may be used to construct expression vectors containing sequences encoding HSLP and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview, N.Y., ch. 4, 8, and 16–17; and Ausubel, F. M. et al. (1995, and periodic supplements) *Current Protocols in Molecular Biology*, John Wiley & Sons, New York, N.Y., ch. 9, 13, and 16.)

A variety of expression vector/host systems may be utilized to contain and express sequences encoding HSLP. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

The "control elements" or "regulatory sequences" are those non-translated regions, e.g., enhancers, promoters, and 5' and 3' untranslated regions, of the vector and polynucleotide sequences encoding HSLP which interact with host cellular proteins to carry out transcription and translation. Such elements may vary in their strength and specificity.

Depending on the vector system and host utilized, any number of suitable transcription and translation elements, including constitutive and inducible promoters, may be used. For example, when cloning in bacterial systems, inducible promoters, e.g., hybrid lacZ promoter of the Bluescript® phagemid (Stratagene, La Jolla, Calif.) or pSport1™ plasmid (GIBCO/BRL), may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HSLP, vectors based on SV40 or EBV may be used with an appropriate selectable marker.

In bacterial systems, a number of expression vectors may be selected depending upon the use intended for HSLP. For example, when large quantities of HSLP are needed for the induction of antibodies, vectors which direct high level expression of fusion proteins that are readily purified may be used. Such vectors include, but are not limited to, multi-functional *E. coli* cloning and expression vectors such as Bluescript® (Stratagene), in which the sequence encoding HSLP may be ligated into the vector in frame with sequences for the amino-terminal Met and the subsequent 7 residues of β-galactosidase so that a hybrid protein is produced, and pIN vectors. (See, e.g., Van Heeke, G. and S. M. Schuster (1989) J. Biol. Chem. 264:5503–5509.) pGEX vectors (Pharmacia Biotech, Uppsala, Sweden) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae*, a number of vectors containing constitutive or inducible promoters, such as alpha factor, alcohol oxidase, and PGH, may be used. (See, e.g., Ausubel, supra; and Grant et al. (1987) Methods Enzymol. 153:516–544.)

In cases where plant expression vectors are used, the expression of sequences encoding HSLP may be driven by any of a number of promoters. For example, viral promoters such as the 35S and 19S promoters of CaMV may be used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. Such techniques are described in a number of generally available reviews. (See, e.g., Hobbs, S. or Murry, L. E. in *McGraw Hill Yearbook of Science and Technology* (1992) McGraw Hill, New York, N.Y.; pp. 191–196.)

An insect system may also be used to express HSLP. For example, in one such system, *Autographa californica* nuclear polyhedrosis virus (AcNPV) is used as a vector to express foreign genes in *Spodoptera frugiperda* cells or in Trichoplusia larvae. The sequences encoding HSLP may be cloned into a non-essential region of the virus, such as the polyhedrin gene, and placed under control of the polyhedrin promoter. Successful insertion of sequences encoding HSLP will render the polyhedrin gene inactive and produce recombinant virus lacking coat protein. The recombinant viruses may then be used to infect, for example, *S. frugiperda* cells or Trichoplusia larvae in which HSLP may be expressed. (See, e.g., Engelhard, E. K. et al. (1994) Proc. Nat. Acad. Sci. 91:3224–3227.)

In mammalian host cells, a number of viral-based expression systems may be utilized. In cases where an adenovirus is used as an expression vector, sequences encoding HSLP may be ligated into an adenovirus transcription/translation complex consisting of the late promoter and tripartite leader sequence. Insertion in a non-essential E1 or E3 region of the viral genome may be used to obtain a viable virus which is capable of expressing HSLP in infected host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of about 6 kb to 10 Mb are constructed and delivered via conventional delivery methods (liposomes, polycationic amino polymers, or vesicles) for therapeutic purposes.

Specific initiation signals may also be used to achieve more efficient translation of sequences encoding HSLP. Such signals include the ATG initiation codon and adjacent sequences. In cases where sequences encoding HSLP and its initiation codon and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers appropriate for the particular cell system used. (See, e.g., Scharf, D. et al. (1994) Results Probl. Cell Differ. 20:125–162.)

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding, and/or function. Different host cells which have specific cellular machinery and characteristic mechanisms for post-translational activities (e.g., CHO, HeLa, MDCK, HEK293, and W138), are available from the American Type Culture Collection (ATCC, Bethesda, Md.) and may be chosen to ensure the correct modification and processing of the foreign protein.

For long term, high yield production of recombinant proteins, stable expression is preferred. For example, cell lines capable of stably expressing HSLP can be transformed using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase genes and adenine phosphoribosyltransferase genes, which can be employed in tk$^-$ or apr$^-$ cells, respectively. (See, e.g., Wigler, M. et al. (1977) Cell 11:223–232; and Lowy, I. et al. (1980) Cell 22:817–823) Also, antimetabolite, antibiotic, or herbicide resistance can be used as the basis for selection. For example, dhfr confers resistance to methotrexate; npt confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB, which allows cells to utilize indole in place of tryptophan, or hisD, which allows cells to utilize histinol in place of histidine. (See, e.g., Hartman, S. C. and R. C. Mulligan (1988) Proc. Natl. Acad. Sci. 85:8047–8051.) Visible markers, e.g., anthocyanins, β glucuronidase and its substrate GUS, luciferase and its substrate luciferin may be used. Green fluorescent proteins (GFP) (Clontech, Palo Alto, Calif.) can also be used. These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding HSLP is inserted within a marker gene sequence, transformed cells containing sequences encoding HSLP can be identified by the absence of marker gene function. Alternatively, a marker gene can be placed in tandem with a sequence encoding HSLP under the control of a single promoter. Expression of the marker gene in response to induction or selection usually indicates expression of the tandem gene as well.

Alternatively, host cells which contain the nucleic acid sequence encoding HSLP and express HSLP may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein sequences.

The presence of polynucleotide sequences encoding HSLP can be detected by DNA-DNA or DNA-RNA hybridization or amplification using probes or fragments or fragments of polynucleotides encoding HSLP. Nucleic acid amplification based assays involve the use of oligonucleotides or oligomers based on the sequences encoding HSLP to detect transformants containing DNA or RNA encoding HSLP.

A variety of protocols for detecting and measuring the expression of HSLP, using either polyclonal or monoclonal antibodies specific for the protein, are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on HSLP is preferred, but a competitive binding assay may be employed. These and other assays are well described in the art. (See, e.g., Hampton, R. et al. (1990) Serological Methods, a Laboratory Manual, APS Press, St Paul, Minn., Section IV; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HSLP include oligolabeling, nick translation, end-labeling, or PCR amplification using a labeled nucleotide. Alternatively, the sequences encoding HSLP, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HSLP may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode HSLP may be designed to contain signal sequences which direct secretion of HSLP through a prokaryotic or eukaryotic cell membrane. Other constructions may be used to join sequences encoding HSLP to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences, such as those specific for Factor XA or enterokinase (Invitrogen, San Diego, Calif.), between the purification domain and the HSLP encoding sequence may be used to facilitate purification. One such expression vector provides for expression of a fusion protein containing HSLP and a nucleic acid encoding 6 histidine residues preceding a thioredoxin or an enterokinase cleavage site. The histidine residues facilitate purification on immobilized metal ion affinity chromatography (IMAC). (See, e.g., Porath, J. et al. (1992) Prot. Exp. Purif. 3: 263–281.) The enterokinase cleavage site provides a means for purifying HSLP from the fusion protein. (See, e.g., Kroll, D. J. et al. (1993) DNA Cell Biol. 12:441–453.) Fragments of HSLP may be produced not only by recombinant production, but also by direct peptide synthesis using solid-phase techniques. (See, e.g., Creighton, T. E. (1984) Protein: Structures and Molecular Properties, pp. 55–60, W. H. Freeman and Co., New York, N.Y.) Protein synthesis may be performed by manual techniques or by automation. Automated synthesis may be achieved, for example, using the Applied Biosystems 431A Peptide Synthesizer (Perkin Elmer). Various fragments of HSLP may be synthesized separately and then combined to produce the full length molecule.

Therapeutics

Chemical and structural homology exists among HSLP and SMN from mouse (GI 1857114) and human (GI 1314346). In addition, HSLP is expressed in reproductive and proliferating tissues. Therefore, HSLP appears to play a role in neurological, reproductive, and cell proliferative disorders.

Therefore, in one embodiment, HSLP or a fragment or derivative thereof may be administered to a subject to treat or prevent a neurological disorder. Such disorders can include, but are not limited to, akathesia, Alzheimer's disease, amnesia, amyotrophic lateral sclerosis, bipolar disorder, catatonia, cerebral neoplasms, dementia, depression, diabetic neuropathy, Down's syndrome, tardive dyskinesia, dystonias, epilepsy, Huntington's disease, peripheral neuropathy, multiple sclerosis, neurofibromatosis, Parkinson's disease, paranoid psychoses, postherpetic neuralgia, schizophrenia, and Tourette's disorder.

In another embodiment, a vector capable of expressing HSLP or a fragment or derivative thereof may be administered to a subject to treat or prevent a neurological disorder including, but not limited to, those described above.

In a further embodiment, a pharmaceutical composition comprising a substantially purified HSLP in conjunction with a suitable pharmaceutical carrier may be administered to a subject to treat or prevent a neurological disorder including, but not limited to, those provided above.

In still another embodiment, an agonist which modulates the activity of HSLP may be administered to a subject to treat or prevent a neurological disorder including, but not limited to, those listed above.

In another embodiment, HSLP or a fragment or derivative thereof may be administered to a subject to treat or prevent a reproductive disorder. Such disorders can include, but are not limited to, abnormal prolactin production, infertility, tubal disease, ovulatory defects, endometriosis, perturbations of the estrous and menstrual cycles, polycystic ovary syndrome, ovarian hyperstimulation syndrome, endometrial and ovarian tumors, autoimmune disorders, ectopic pregnancy, teratogenesis, breast cancer, fibrocystic breast disease, galactorrhea, abnormal spermatogenesis, abnormal sperm physiology, testicular cancer, prostate cancer, benign prostatic hyperplasia, prostatitis, and gynecomastia.

In another embodiment, a vector capable of expressing HSLP or a fragment or derivative thereof may be administered to a subject to treat or prevent a reproductive disorder including, but not limited to, those described above.

In a further embodiment, a pharmaceutical composition comprising a substantially purified HSLP in conjunction with a suitable pharmaceutical carrier may be administered to a subject to treat or prevent a reproductive disorder including, but not limited to, those provided above.

In still another embodiment, an agonist which modulates the activity of HSLP may be administered to a subject to treat or prevent a reproductive disorder including, but not limited to, those listed above.

In a further embodiment, an antagonist of HSLP may be administered to a subject to treat or prevent a cell proliferative disorder. Such disorders may include, but are not limited to, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds HSLP may be used directly as an antagonist or indirectly as a targeting or delivery mechanism for bringing a pharmaceutical agent to cells or tissue which express HSLP.

In an additional embodiment, a vector expressing the complement of the polynucleotide encoding HSLP may be administered to a subject to treat or prevent a cell proliferative disorder including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HSLP may be produced using methods which are generally known in the art. In particular, purified HSLP may be used to produce antibodies or to screen libraries of pharmaceutical agents to identify those which specifically bind HSLP. Antibodies to HSLP may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with HSLP or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HSLP have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of HSLP amino acids may be fused with those of another protein, such as KLH, and antibodies to the chimeric molecule may be produced.

Monoclonal antibodies to HSLP may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce HSLP-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; and Winter, G. et al. (1991) Nature 349:293–299.)

Antibody fragments which contain specific binding sites for HSLP may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HSLP and its specific antibody. A two-site, monoclonal-based immunoassay utilizing monoclonal antibodies reactive to two non-interfering HSLP epitopes is preferred, but a competitive binding assay may also be employed. (Maddox, supra.)

In another embodiment of the invention, the polynucleotides encoding HSLP, or any fragment or complement thereof, may be used for therapeutic purposes. In one aspect, the complement of the polynucleotide encoding HSLP may be used in situations in which it would be desirable to block the transcription of the mRNA. In particular, cells may be transformed with sequences complementary to polynucleotides encoding HSLP. Thus, complementary molecules or fragments may be used to modulate HSLP activity, or to achieve regulation of gene function. Such technology is now well known in the art, and sense or antisense oligonucleotides or larger fragments can be designed from various locations along the coding or control regions of sequences encoding HSLP.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequences complementary to the polynucleotides of the gene encoding HSLP. (See, e.g., Sambrook, supra; and Ausubel, supra.)

Genes encoding HSLP can be turned off by transforming a cell or tissue with expression vectors which express high levels of a polynucleotide, or fragment thereof, encoding HSLP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding HSLP. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding HSLP.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HSLP. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of HSLP, antibodies to HSLP, and mimetics, agonists, antagonists, or inhibitors of HSLP. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of HSLP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example HSLP or fragments thereof, antibodies of HSLP, and agonists, antagonists or inhibitors of HSLP, which ameliorates the symptoms or condition. Therapeutic efficacy and toxicity may be determined by standard pharmaceutical procedures in cell cultures or with experimental animals, such as by calculating the ED50 (the dose therapeutically effective in 50% of the population) or LD50 (the dose lethal to 50% of the population) statistics. The dose ratio of therapeutic to toxic effects is the therapeutic index, and it can be expressed as the ED50/LD50 ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the ED50 with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 $\mu$g to 100,000 $\mu$g, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HSLP may be used for the diagnosis of disorders characterized by expression of HSLP, or in assays to monitor patients being treated with HSLP or agonists, antagonists, or inhibitors of HSLP. Antibodies useful for diagnostic purposes may be prepared in the same manner as described above for therapeutics. Diagnostic assays for HSLP include methods which utilize the antibody and a label to detect HSLP in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring HSLP, including ELISAs, RIAs, and FACS, are known in the art and provide a basis for diagnosing altered or abnormal levels of HSLP expression. Normal or standard values for HSLP expression are established by combining body fluids or cell extracts taken from normal mammalian subjects, preferably human, with antibody to HSLP under conditions suitable for complex formation The amount of standard complex formation may be quantitated by various methods, preferably by photometric means. Quantities of HSLP expressed in subject, control, and disease samples from biopsied tissues are compared with the standard values. Deviation between standard and subject values establishes the parameters for diagnosing disease.

In another embodiment of the invention, the polynucleotides encoding HSLP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HSLP may be correlated with disease. The diagnostic assay may be used to determine absence, presence, and excess expression of HSLP, and to monitor regulation of HSLP levels during therapeutic intervention.

In one aspect, hybridization with PCR probes which are capable of detecting polynucleotide sequences, including genomic sequences, encoding HSLP or closely related molecules may be used to identify nucleic acid sequences which encode HSLP. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding HSLP, alleles, or related sequences.

Probes may also be used for the detection of related sequences, and should preferably have at least 50% sequence identity to any of the HSLP encoding sequences. The hybridization probes of the subject invention may be DNA or RNA and may be derived from the sequence of SEQ ID NO:2 or from genomic sequences including promoters, enhancers, and introns of the HSLP gene.

Means for producing specific hybridization probes for DNAs encoding HSLP include the cloning of polynucleotide sequences encoding HSLP or HSLP derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}$P or $^{35}$S, or by enzymatic labels, such as alkaline phosphatase coupled to the probe via avidin/biotin coupling systems, and the like.

Polynucleotide sequences encoding HSLP may be used for the diagnosis of a disorder associated with expression of HSLP. Examples of such a disorder include, but are not limited to, a neurological disorder such as akathesia, Alzheimer's disease, amnesia, amyotrophic lateral sclerosis, bipolar disorder, catatonia, cerebral neoplasms, dementia, depression, diabetic neuropathy, Down's syndrome, tardive dyskinesia, dystonias, epilepsy, Huntington's disease, peripheral neuropathy, multiple sclerosis, neurofibromatosis, Parkinson's disease, paranoid psychoses, postherpetic neuralgia, schizophrenia, and Tourette's disorder; a reproductive disorder such as abnormal prolactin production, infertility, tubal disease, ovulatory defects, endometriosis, perturbations of the estrous and menstrual cycles, polycystic ovary syndrome, ovarian hyperstimulation syndrome, endometrial and ovarian tumors, autoimmune disorders, ectopic pregnancy, teratogenesis, breast cancer, fibrocystic breast disease, galactorrhea, abnormal spermatogenesis, abnormal sperm physiology, testicular cancer, prostate cancer, benign prostatic hyperplasia, prostatitis, and gynecomastia; and a cell proliferative disorder such as arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. The polynucleotide sequences encoding HSLP may be used in Southern or northern analysis, dot blot, or other membrane-based technologies; in PCR technologies; in dipstick, pin, and ELISA assays; and in microarrays utilizing fluids or tissues from patients to detect altered HSLP expression. Such qualitative or quantitative methods are well known in the art.

In a particular aspect, the nucleotide sequences encoding HSLP may be useful in assays that detect the presence of associated disorders, particularly those mentioned above. The nucleotide sequences encoding HSLP may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding HSLP in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of HSLP, a normal or standard profile for expression is established. This may be accomplished by combining body fluids or cell extracts taken from normal subjects, either animal or human, with a sequence, or a fragment thereof, encoding HSLP, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HSLP may involve the use of PCR. These oligomers may be chemically synthesized, generated enzymatically, or produced in vitro. Oligomers will preferably contain a fragment of a polynucleotide encoding HSLP, or a fragment of a polynucleotide complementary to the polynucleotide encoding HSLP, and will be employed under optimized conditions for identification of a specific gene or condition. Oligomers may also be employed under less stringent conditions for detection or quantitation of closely related DNA or RNA sequences.

Methods which may also be used to quantitate the expression of HSLP include radiolabeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 229–236.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding HSLP may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial PI constructions, or single chromosome cDNA libraries. (See, e.g., Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and Biotechnology*, VCH Publishers New York, N.Y., pp. 965–968.) Examples of genetic map data can be found in various scientific journals or at the Online Mendelian Inheritance in Man (OMIM) site. Correlation between the location of the gene encoding HSLP on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., AT to 11q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, HSLP, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between HSLP and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with HSLP, or fragments thereof, and washed. Bound HSLP is then detected by methods well known in the art. Purified HSLP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HSLP specifically compete with a test compound for binding HSLP. In this manner, antibodies can be used to detect the presence of any peptide which shares one or more antigenic determinants with HSLP.

In additional embodiments, the nucleotide sequences which encode HSLP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. BRSTNOT24 cDNA Library Construction

The BRSTNOT24 cDNA library was constructed from diseased breast tissue removed from a 46-year-old Caucasian female during bilateral subcutaneous mammectomy, bilateral breast augmentation, and total breast reconstruction. Pathology indicated benign fibrocystic disease bilaterally. The patient presented with fibrosclerosis of the breast. Family history included breast cancer in the mother and sibling.

The frozen tissue was homogenized and lysed in TRIzol reagent (1 gm tissue/10 ml TRIzol; Catalog #10296-028, Gibco/BRL, Gaithersburg, Md.), a monoplastic solution of phenol and guanidine isothiocyanate, using a Brinkmann Homogenizer Polytron PT-3000 (Brinkmann Instruments, Westbury, N.Y.). After brief incubation on ice, chloroform was added (1:5 v/v), and the mixture was centrifuged to separate the phases. The upper aqueous phase was removed to a fresh tube, and isopropanol was added to precipitate RNA. The RNA was resuspended in RNase-free water and treated with DNase. The RNA was re-extracted once with acid phenol-chloroform and reprecipitated with sodium acetate and ethanol. Poly(A+) RNA was isolated using the Qiagen Oligotex kit (QIAGEN, Chatsworth, Calif.).

Poly (A+) RNA was used to construct the BRSTNOT24 cDNA library according to the recommended protocols in the SuperScript Plasmid System (Catalog #18248-013, Gibco/BRL). The cDNAs were fractionated on a Sepharose CL4B column (Catalog #275105-01, Pharmacia, Piscataway, N.J.), and those cDNAs exceeding 400 bp were ligated into the plasmid pINCY 1 (Incyte). pINCY 1 was subsequently transformed into DH5α™ competent cells (Catalog #18258-012, Gibco/BRL).

II. Isolation and Sequencing of cDNA Clones

Plasmid DNA was released from the cells and purified using the REAL Prep 96 plasmid kit (Catalog #26173, QIAGEN). The recommended protocol was employed except for the following changes: 1) the bacteria were cultured in 1 ml of sterile Terrific Broth (Catalog #22711, Gibco/BRL) with carbenicillin at 25 mg/L and glycerol at 0.4%; 2) after the cultures were incubated for 19 hours, the cells were lysed with 0.3 ml of lysis buffer; and 3) following isopropanol precipitation, the plasmid DNA pellets were each resuspended in 0.1 ml of distilled water. The DNA samples were stored at 4° C.

The cDNAs were sequenced by the method of Sanger et al. (1975, J. Mol. Biol. 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems.

III. Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST (Basic Local Alignment Search Tool). (See, e.g., Altschul, S. F. (1993) J. Mol. Evol 36:290–300; and Altschul et al. (1990) J. Mol. Biol. 215:403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms could have been used when dealing with primary sequence patterns and secondary structure gap penalties. (See, e.g., Smith, T. et al. (1992) Protein Engineering 5:35–51.) The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-8}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for homology.

Additionally, sequences identified from cDNA libraries may be analyzed to identify those gene sequences encoding conserved protein motifs using an appropriate analysis program, e.g., the Block 2 Bioanalysis Program (Incyte, Palo Alto, Calif.). This motif analysis program, based on sequence information contained in the Swiss-Prot Database and PROSITE, is a method of determining the function of uncharacterized proteins translated from genomic or cDNA sequences. (See, e.g., Bairoch, A. et al. (1997) Nucleic Acids Res. 25:217–221; and Attwood, T. K. et al. (1997) J. Chem. Inf. Comput. Sci. 37:417–424.) PROSITE may be used to identify common functional or structural domains in divergent proteins. The method is based on weight matrices. Motifs identified by this method are then calibrated against the SWISS-PROT database in order to obtain a measure of the chance distribution of the matches.

In another alternative, Hidden Markov models (HMMs) may be used to find protein domains, each defined by a dataset of proteins known to have a common biological function. (See, e.g., Pearson, W. R. and D. J. Lipman (1988) Proc. Natl. Acad. Sci. 85:2444–2448; and Smith, T. F. and M. S. Waterman (1981) J. Mol. Biol. 147:195–197.) HMMs were initially developed to examine speech recognition patterns, but are now being used in a biological context to analyze protein and nucleic acid sequences as well as to model protein structure. (See, e.g., Krogh, A. et al. (1994) J. Mol. Biol. 235:1501–1531; and Collin, M. et al. (1993) Protein Sci. 2:305–314.) HMMs have a formal probabilistic basis and use position-specific scores for amino acids or nucleotides. The algorithm continues to incorporate information from newly identified sequences to increase its motif analysis capabilities.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, F. M. et al. supra, ch. 4 and 16.)

Analogous computer techniques applying BLAST are used to search for identical or related molecules in nucleotide databases such as GenBank or LIFESEQ™ database (Incyte Pharmaceuticals). This analysis is much faster than multiple membrane-based hybridizations. In addition, the sensitivity of the computer search can be modified to determine whether any particular match is categorized as exact or homologous.

The basis of the search is the product score, which is defined as:

% sequence identity×% maximum BLAST score/100

The product score takes into account both the degree of similarity between two sequences and the length of the sequence match. For example, with a product score of 40, the match will be exact within a 1% to 2% error, and, with a product score of 70, the match will be exact. Homologous molecules are usually identified by selecting those which show product scores between 15 and 40, although lower scores may identify related molecules.

The results of northern analysis are reported as a list of libraries in which the transcript encoding HSLP occurs. Abundance and percent abundance are also reported. Abundance directly reflects the number of times a particular transcript is represented in a cDNA library, and percent abundance is abundance divided by the total number of sequences examined in the cDNA library.

V. Extension of HSLP Encoding Polynucleotides

The nucleic acid sequence of Incyte Clone 3769729 was used to design oligonucleotide primers for extending a partial nucleotide sequence to full length. One primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 (National Biosciences, Plymouth, Minn.), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (GIBCO/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. PCR was performed using the Peltier Thermal Cycler (PTC200; M.J. Research, Watertown, Mass.), beginning with 40 pmol of each primer and the recommended concentrations of all other components of the kit, with the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQuick™ (QIAGEN Inc., Chatsworth, Calif.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2 to 3 hours, or overnight at 16° C. Competent E. coli cells (in 40 µl of appropriate media) were transformed with 3 µl of ligation mixture and cultured in 80 µl of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1) containing 2× Carb. The following day, several colonies were randomly picked from each plate and cultured in 150 μl of liquid LB/2× Carb medium placed in an individual well of an appropriate commercially-available sterile 96-well microtiter plate. The following day, 5 μl of each overnight culture was transferred into a non-sterile 96-well plate and, after dilution 1:10 with water, 5 μl from each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 (National Biosciences) and labeled by combining 50 pmol of each oligomer, 250 μCi of [γ-$^{32}$P] adenosine triphosphate (Amersham, Chicago, Ill.), and T4 polynucleotide kinase (DuPont NEN®, Boston, Mass.). The labeled oligonucleotides are substantially purified using a Sephadex G-25 superfine resin column (Pharmacia & Upjohn, Kalamazoo, Mich.). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba 1, or Pvu II (DuPont NEN, Boston, Mass.).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester, N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE™. Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; and Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the HSLP-encoding sequences, or any parts thereof, are used to detect, decrease, or inhibit expression of naturally occurring HSLP. Although use of oligonucleotides comprising from about 15 to 30 base pairs is described, essentially the same procedure is used with smaller or with larger sequence fragments. Appropriate oligonucleotides are designed using Oligo 4.06 software and the coding sequence of HSLP. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HSLP-encoding transcript.

IX. Expression of HSLP

Expression of HSLP is accomplished by subcloning the cDNA into an appropriate vector and transforming the vector into host cells. This vector contains an appropriate promoter, e.g., β-galactosidase, upstream of the cloning site, operably associated with the cDNA of interest. (See, e.g., Sambrook, supra, pp. 404–433; and Rosenberg, M. et al. (1983) Methods Enzymol. 101:123–138.)

Induction of an isolated, transformed bacterial strain with isopropyl beta-D-thiogalactopyranoside (IPTG) using standard methods produces a fusion protein which consists of the first 8 residues of β-galactosidase, about 5 to 15 residues of linker, and the full length protein. The signal residues direct the secretion of HSLP into bacterial growth media which can be used directly in the following assay for activity.

X. Demonstration of HSLP Activity

An assay for HSLP activity measures its affinity for proteins involved in RNA processing. The yeast two-hybrid system is a sensitive, enzymatic method for detection of protein-protein interactions in vivo. This method is used to identify SMN-interacting proteins (Liu and Dreyfuss, supra.) and is well known by those skilled in the art. Recombinant DNA methods are used to express HSLP, fibrillarin, and the RGG RNA-binding motif of hnRNP U (RGG) in the yeast *Saccharomyces cerevisiae*. These proteins are expressed as fusions with other polypeptide fragments involved in gene regulation. The interaction of HSLP with either fibrillarin or RGG triggers the expression of a reporter gene. This gene encodes a metabolic enzyme that generates a colored reaction product. When plated on the appropriate substratum, the yeast will turn from white to blue in color. The amount of reaction product can be quantified spectrophotometrically and is proportional to the affinity of HSLP for either fibrillarin or RGG.

XI. Production of HSLP Specific Antibodies

HSLP substantially purified using PAGE electrophoresis (see, e.g., Harrington, M. G. (1990) Methods Enzymol. 182:488–495), or other purification techniques, is used to immunize rabbits and to produce antibodies using standard protocols. The HSLP amino acid sequence is analyzed using DNASTAR software (DNASTAR Inc) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel et al. supra, ch. 11.)

Typically, the oligopeptides are 15 residues in length, and are synthesized using an Applied Biosystems Peptide Synthesizer Model 431A using fmoc-chemistry and coupled to KLH (Sigma, St. Louis, Mo.) by reaction with N-maleimidobenzoyl-N-hydroxysuccinimide ester (MBS) to increase immunogenicity. (See, e.g., Ausubel et al. supra.) Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radio-iodinated goat anti-rabbit IgG.

XII. Purification of Naturally Occurring HSLP Using Specific Antibodies

Naturally occurring or recombinant HSLP is substantially purified by immunoaffinity chromatography using antibodies specific for HSLP. An immunoaffinity column is constructed by covalently coupling anti-HSLP antibody to an activated chromatographic resin, such as CNBr-activated Sepharose (Pharmacia & Upjohn). After the coupling, the resin is blocked and washed according to the manufacturer's instructions.

Media containing HSLP are passed over the immunoaffinity column, and the column is washed under conditions that allow the preferential absorbance of HSLP (e.g., high ionic strength buffers in the presence of detergent). The column is eluted under conditions that disrupt antibody/HSLP binding (e.g., a buffer of pH 2 to pH 3, or a high concentration of a chaotrope, such as urea or thiocyanate ion), and HSLP is collected.

XIII. Identification of Molecules Which Interact with HSLP

HSLP, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled HSLP, washed, and any wells with labeled HSLP complex are assayed. Data obtained using different concentrations of HSLP are used to calculate values for the number, affinity, and association of HSLP with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 238 amino acids
      (B) TYPE: amino acid
      (C) STRANDEDNESS: single
      (D) TOPOLOGY: linear (vii) IMMEDIATE SOURCE:
      (A) LIBRARY: BRSTNOT24
      (B) CLONE: 3769729

(xi) SEQUENCE DESCRIPTION: SEQ ID NO:1:

```
Met Ser Glu Asp Leu Ala Lys Gln Leu Ala Ser Tyr Lys Ala Gln Leu
 1               5                  10                  15

Gln Gln Val Glu Ala Ala Leu Ser Gly Asn Gly Glu Asn Glu Asp Leu
            20                  25                  30

Leu Lys Leu Lys Lys Asp Leu Gln Glu Val Ile Glu Leu Thr Lys Asp
        35                  40                  45

Leu Leu Ser Thr Gln Pro Ser Glu Thr Leu Ala Ser Ser Asp Ser Phe
    50                  55                  60
```

-continued

```
Ala Ser Thr Gln Pro Thr His Ser Trp Lys Val Gly Asp Lys Cys Met
 65                  70                  75                  80

Ala Val Trp Ser Glu Asp Gly Gln Cys Tyr Glu Ala Glu Ile Glu Glu
                 85                  90                  95

Ile Asp Glu Glu Asn Gly Thr Ala Ala Ile Thr Phe Ala Gly Tyr Gly
            100                 105                 110

Asn Ala Glu Val Thr Pro Leu Leu Asn Leu Lys Pro Val Glu Glu Gly
        115                 120                 125

Arg Lys Ala Lys Glu Asp Ser Gly Asn Lys Pro Met Ser Lys Lys Glu
    130                 135                 140

Met Ile Ala Gln Gln Arg Glu Tyr Lys Lys Lys Ala Leu Lys Lys
145                 150                 155                 160

Ala Gln Arg Ile Lys Glu Leu Glu Gln Glu Arg Glu Asp Gln Lys Val
                165                 170                 175

Lys Trp Gln Gln Phe Asn Asn Arg Ala Tyr Ser Lys Asn Lys Lys Gly
            180                 185                 190

Gln Val Lys Arg Ser Ile Phe Ala Ser Pro Glu Ser Val Thr Gly Lys
        195                 200                 205

Val Gly Val Gly Thr Cys Gly Ile Ala Asp Lys Pro Met Thr Gln Tyr
    210                 215                 220

Gln Asp Thr Ser Lys Tyr Asn Val Arg His Leu Met Pro Gln
225                 230                 235
```

(2) INFORMATION FOR SEQ ID NO:2:

(i) SEQUENCE CHARACTERISTICS:
        (A) LENGTH: 2426 base pairs
        (B) TYPE: nucleic acid
        (C) STRANDEDNESS: single
        (D) TOPOLOGY: linear (vii) IMMEDIATE SOURCE:
        (A) LIBRARY: BRSTNOT24
        (B) CLONE: 3769729

(xi) SEQUENCE DESCRIPTION: SEQ ID NO:2:

```
TCTTTCATAG AGACTAAAGT TATTCAGCAG GCAGCAAAAT AATCTACTTA AGTCCTGCCT      60

TTCTTTTTTC ACTTAAAAAA GTGGGTGTGA TAATATCCAG GCTAGCTAGC TGACTAGCTC     120

CCCGGGCAGT CTATGATAAT CAGAGATAGT CAATTTATTA GGCTGTTTTG CTGAATAAGC     180

TGGTTCTAAA GGAGGCAGGG GTCAAGTCAC TTGTCTCATA TATTACAGTG GCTCTCTGCA     240

TCCCCGAAAC GCCTTCCTTC AGTAAGCAGA GTGCTTGAGT GCACCCCATT TGACCTGCTG     300

ATATGTAGAT CACAACNCCT GATGCTTCCT GGAATTGCCG ATTACTGTAA CTGCTGCCCA     360

TCTGTCGATG AAGGAGCAGT TTCAGAACTC AGACTTGAGG GAGGAAAAGT AATTAATGGT     420

GCCCGGCGTT CCTCCCTTCC CCCTCGCCGC CGACCGAGTT CTTCCTTTTC AGACCGGGTC     480

GCCTTGCTGT CGTCGCGGTG ATTTTCCTGC TACTGCTACT GCTGCTGCTG CCACCGCCAC     540

TACCACTGGG CTCATTTGCC CCGACCCCTT CCCGCCGCCC CGCCCCCAGC CCACACAAG      600

ATGTCAGAGG ATTTAGCAAA GCAGCTGGCA AGCTACAAAG CTCAGCTCCA GCAAGTTGAA     660

GCTGCATTAT CTGGAAATGG AGAAAATGAA GATTTGCTAA AATTGAAGAA AGATTTACAA     720

GAAGTTATAG AACTAACCAA AGACCTTCTG TCAACTCAAC CTTCTGAGAC GCTTGCAAGT     780

TCAGACAGTT TTGCTTCTAC TCAACCTACT CATTCATGGA AAGTAGGAGA CAAGTGTATG     840

GCAGTCTGGA GTGAAGATGG ACAGTGTTAT GAAGCGGAGA TTGAGGAGAT AGATGAAGAA     900

AATGGCACCG CTGCAATCAC CTTTGCTGGT TATGGCAATG CTGAAGTGAC TCCACTGTTG     960
```

```
AACCTCAAGC CTGTAGAAGA AGGAAGGAAG GCAAAGGAGG ACAGTGGCAA CAAACCCATG    1020

TCAAAAAAAG AAATGATTGC CCAGCAGCGT GAATATAAAA AGAAGAAAGC TTTGAAAAAA    1080

GCTCAGAGAA TAAAGAACT  TGAGCAGGAA AGAGAGGACC AGAAAGTGAA ATGGCAACAA    1140

TTCAACAACA GAGCCTATTC TAAAAACAAA AAAGGCCAGG TAAAGAGGAG TATTTTTGCT    1200

TCACCTGAGA GTGTGACTGG TAAAGTTGGA GTAGGAACCT GTGGAATTGC TGATAAACCT    1260

ATGACACAAT ATCAAGATAC CTCTAAATAC AATGTCAGGC ATTTGATGCC TCAATAATCA    1320

GAAAAACTGT TGGATTTCAT CTCTGCAGGG CTTTACATTT ACCTTTTTAT CCTTATATTT    1380

TTCTAAAGGT AAATTATTTG TTAGATGAGT AAGCAAGATA CCATTGTCGT CATTGGTTGG    1440

CTTCAGTAGA ATGAAACGTG AAGAAATTGC ATTTGATAAC TGCTATTCAT TTAACTTTTC    1500

TCATTATCAG TACCACGGTT CCCTCAAAGT TTGTTGAATA AAGCAACTTT TGTAGATGCT    1560

GTTTCATACA GCACTTAGAT GAATTATTGA TCTTCCTAAT ATCAGGCGCC TACTTAACCT    1620

ATGGTGTGTA CTTTTTGTAA GTTGTAACTT GAAATTTTCA GATGCTTTGA ACTTGACACA    1680

TACTCTAGCA ATTCATTGGA ACACCAAGGC AAAAACACCA ACCTGCTAAA AGAGATCTTT    1740

TCATTTTTCT TATTTTCAGC TTTAAAACTT AGCTGTCGTT CAGTTAAGCT TAAAGATAGG    1800

TTAATTTGTA AATGGCAAAG TTTGTTTTGA GGTTTTTCCT CAATAACTTG TTTCCCAGGC    1860

CTATTAGGCC ATCTCTAAAA TTGATCTAGC TGTTTTATTT TTATGTACTC TTAGTTTTAT    1920

GTAAGAAACC TTAGGATGAG CTCCCTTTTC TAAGGTGTTT TTGTTTTTTG TATGTTTGCT    1980

TTTTTCCTGT TTTTTGTTTT TTCCATTTAC GGCAGTGGTA CCATGTTTTG GATGTGTGAT    2040

GTTTATATGG GAGAACAAAA AGCTGATGTA TAGCCCTGTA TACAGTGTAG ATACTATTTT    2100

TGTAAAAACA CAAGGCTAAA TTAATGAACA AGAATACTGA ATATTTCATC ATTAAAAATT    2160

TCTTGTATTT CTTGTGCATT AATCTGACGA TAATTTCCCT GTATATTATG TTCATTTAGC    2220

TGTTTGTAAT TTTTGTTAAT TAGATCAGGT TGTCTGCATT TGTTGGTGTA AGTGAACATC    2280

ATCACAGTTA TCCTGAGTTG AGTTTAAGCC AAATACATGC ATAGAAAAGG GTCTTCCTAT    2340

TAATGGAAGA AGGTAATTTT TAGGATGTGT ATTATTTCAG TTTTGTATGT TTAACTTTTA    2400

TTAAATAAAG TGTTTTTAAA ATCTCC                                         2426

(2) INFORMATION FOR SEQ ID NO:3:

(i) SEQUENCE CHARACTERISTICS:
        (A) LENGTH: 288 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1857114

(xi) SEQUENCE DESCRIPTION: SEQ ID NO:3:

Met Ala Met Gly Ser Gly Gly Ala Gly Ser Glu Gln Glu Asp Thr Val
  1               5                  10                  15

Leu Phe Arg Arg Gly Thr Gly Gln Ser Asp Asp Ser Asp Ile Trp Asp
                 20                  25                  30

Asp Thr Ala Leu Ile Lys Ala Tyr Asp Lys Ala Val Ala Ser Phe Lys
             35                  40                  45

His Ala Leu Lys Asn Gly Asp Ile Cys Glu Thr Pro Asp Lys Pro Lys
         50                  55                  60

Gly Thr Ala Arg Arg Lys Pro Ala Lys Lys Asn Lys Ser Gln Lys Lys
```

-continued

```
            65                  70                  75                  80
Asn Ala Thr Thr Pro Leu Lys Gln Trp Lys Val Gly Asp Lys Cys Ser
                     85                  90                  95

Ala Val Trp Ser Glu Asp Gly Cys Ile Tyr Pro Ala Thr Ile Thr Ser
                100                 105                 110

Ile Asp Phe Lys Arg Glu Thr Cys Val Val Tyr Thr Gly Tyr Gly
            115                 120                 125

Asn Arg Glu Glu Gln Asn Leu Ser Asp Leu Leu Ser Pro Thr Cys Glu
        130                 135                 140

Val Ala Asn Ser Thr Glu Gln Asn Thr Gln Glu Asn Glu Ser Gln Val
145                 150                 155                 160

Ser Thr Asp Asp Ser Glu His Ser Ser Arg Ser Leu Arg Ser Lys Ala
                165                 170                 175

His Ser Lys Ser Lys Ala Ala Pro Trp Thr Ser Phe Leu Pro Pro Pro
            180                 185                 190

Pro Pro Met Pro Gly Ser Gly Leu Gly Pro Gly Lys Pro Gly Leu Lys
        195                 200                 205

Phe Asn Gly Pro Pro Pro Pro Pro Leu Pro Pro Pro Phe Leu
210                 215                 220

Pro Cys Trp Met Pro Pro Phe Pro Ser Gly Pro Pro Ile Ile Pro Pro
225                 230                 235                 240

Pro Pro Pro Ile Ser Pro Asp Cys Leu Asp Asp Thr Asp Ala Leu Gly
            245                 250                 255

Ser Met Leu Ile Ser Trp Tyr Met Ser Gly Tyr His Thr Gly Tyr Tyr
                260                 265                 270

Met Gly Phe Arg Gln Asn Lys Lys Glu Gly Lys Cys Ser His Thr Asn
            275                 280                 285

(2) INFORMATION FOR SEQ ID NO:4:

(i) SEQUENCE CHARACTERISTICS:
        (A) LENGTH: 294 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1314346

(xi) SEQUENCE DESCRIPTION: SEQ ID NO:4:

Met Ala Met Ser Ser Gly Gly Ser Gly Gly Gly Val Pro Glu Gln Glu
1               5                   10                  15

Asp Ser Val Leu Phe Arg Arg Gly Thr Gly Gln Ser Asp Asp Ser Asp
            20                  25                  30

Ile Trp Asp Asp Thr Ala Leu Ile Lys Ala Tyr Asp Lys Ala Val Ala
        35                  40                  45

Ser Phe Lys His Ala Leu Lys Asn Gly Asp Ile Cys Glu Thr Ser Gly
    50                  55                  60

Lys Pro Lys Thr Thr Pro Lys Arg Lys Pro Ala Lys Lys Asn Lys Ser
65                  70                  75                  80

Gln Lys Lys Asn Thr Ala Ala Ser Leu Gln Gln Trp Lys Val Gly Asp
            85                  90                  95

Lys Cys Ser Ala Ile Trp Ser Glu Asp Gly Cys Ile Tyr Pro Ala Thr
        100                 105                 110

Ile Ala Ser Ile Asp Phe Lys Arg Glu Thr Cys Val Val Tyr Thr
    115                 120                 125
```

-continued

```
Gly Tyr Gly Asn Arg Glu Glu Gln Asn Leu Ser Asp Leu Leu Ser Pro
    130                 135                 140

Ile Cys Glu Val Ala Asn Asn Ile Glu Gln Asn Ala Gln Glu Asn Glu
145                 150                 155                 160

Asn Glu Ser Gln Val Ser Thr Asp Glu Ser Glu Asn Ser Arg Ser Pro
                165                 170                 175

Gly Asn Lys Ser Asp Asn Ile Lys Pro Lys Ser Ala Pro Trp Asn Ser
                180                 185                 190

Phe Leu Pro Pro Pro Pro Met Pro Gly Pro Arg Leu Gly Pro Gly
        195                 200                 205

Lys Pro Gly Leu Lys Phe Asn Gly Pro Pro Pro Pro Pro Pro Pro
    210                 215                 220

Pro Pro His Leu Leu Ser Cys Trp Leu Pro Pro Phe Pro Ser Gly Pro
225                 230                 235                 240

Pro Ile Ile Pro Pro Pro Pro Pro Ile Cys Pro Asp Ser Leu Asp Asp
                245                 250                 255

Ala Asp Ala Leu Gly Ser Met Leu Ile Ser Trp Tyr Met Ser Gly Tyr
                260                 265                 270

His Thr Gly Tyr Tyr Met Gly Phe Arg Gln Asn Gln Lys Glu Gly Arg
        275                 280                 285

Cys Ser His Ser Leu Asn
        290
```

What is claimed is:

1. An isolated and purified polynucleotide encoding a polypeptide comprising the amino acid sequence of SEQ ID NO:1.

2. An isolated and purified polynucleotide which is completely complementary to the polynucleotide of claim 1.

3. An expression vector comprising the polynucleotide of claim 1.

4. An isolated host cell comprising the expression vector of claim 3.

5. A method for producing a polypeptide comprising the amino acid sequence of SEQ ID NO:1, the method comprising the steps of:

(a) culturing the isolated host cell of claim 4 under conditions suitable for the expression of the polypeptide; and (b) recovering the polypeptide from the host cell culture.

6. An isolated and purified polynucleotide comprising the polynucleotide sequence of SEQ ID NO:2.

7. An isolated and purified polynucleotide which is completely complementary to the polynucleotide of claim 6.

* * * * *